(12) United States Patent
Zhao et al.

(10) Patent No.: US 9,465,189 B2
(45) Date of Patent: Oct. 11, 2016

(54) OPTICAL PROBE

(71) Applicant: NUCTECH COMPANY LIMITED, Beijing (CN)

(72) Inventors: Ziran Zhao, Beijing (CN); Jianhong Zhang, Beijing (CN); Hongqiu Wang, Beijing (CN); Dong Lin, Beijing (CN); Shixin Zhang, Beijing (CN); Bin Hu, Beijing (CN); Yumin Yi, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 114 days.

(21) Appl. No.: 14/573,387

(22) Filed: Dec. 17, 2014

(65) Prior Publication Data

US 2015/0185431 A1    Jul. 2, 2015

(30) Foreign Application Priority Data

Dec. 27, 2013 (CN) .......................... 2013 1 0741550

(51) Int. Cl.
| | |
|---|---|
| *G02B 7/02* | (2006.01) |
| *G02B 7/04* | (2006.01) |
| *G02B 7/32* | (2006.01) |
| *G01N 21/01* | (2006.01) |
| *G01N 21/63* | (2006.01) |

(52) U.S. Cl.
CPC ................. *G02B 7/04* (2013.01); *G01N 21/01* (2013.01); *G01N 21/63* (2013.01); *G02B 7/022* (2013.01); *G02B 7/32* (2013.01); *G01N 2201/02* (2013.01)

(58) Field of Classification Search
CPC ...... G01N 21/01; G01N 21/62; G01N 21/63; G01N 2201/02; G02B 7/04; G02B 7/02; G02B 7/022; G02B 7/32; G11B 7/0917; G03F 7/70641

USPC ........................ 359/819, 822, 823, 825, 826; 385/31–33; 250/201.5, 234

See application file for complete search history.

(56) References Cited

U.S. PATENT DOCUMENTS

| 4,003,059 A | * | 1/1977 | Sugiura | ............... | G11B 7/08582 347/257 |
|---|---|---|---|---|---|
| 5,136,149 A | * | 8/1992 | Fujiwara | ................... | G02B 7/32 250/201.5 |
| 5,351,264 A | * | 9/1994 | Kato | ......................... | G11B 7/22 372/101 |
| 5,804,805 A | * | 9/1998 | Koenck | .............. | G06K 7/10574 235/462.01 |
| 5,841,121 A | * | 11/1998 | Koenck | .............. | G06K 7/10574 235/472.01 |

* cited by examiner

*Primary Examiner* — Loha Ben
(74) *Attorney, Agent, or Firm* — Westerman, Hattori, Daniels & Adrian, LLP

(57) ABSTRACT

An embodiment of the present invention provides an optical probe, comprising: a first sleeve in which a lens is contained, the first sleeve having a light transmission aperture from which an exciting light enters the first sleeve; a second sleeve movably engaged with the first sleeve and having a detection window from which the exciting light having passed through the first sleeve and focused by the lens exits the optical probe, the second sleeve being capable of moving with respect to the first sleeve from a first detection position to a second detection position or from the second detection position to the first detection position; and a positioning member configured to position the second sleeve at the first detection position or the second detection position with respect to the first sleeve.

10 Claims, 5 Drawing Sheets

OPTICAL PROBE

CROSS-REFERENCE TO RELATED APPLICATION

This application claims the benefit of Chinese Patent Application No. 201310741550.4 filed on Dec. 27, 2013 in the State Intellectual Property Office of China, the whole disclosure of which is incorporated herein by reference.

BACKGROUND OF THE INVENTION

1. Field of the Invention

The present disclosure relates to the field of optical inspection, and more particularly, to an optical probe.

2. Description of the Related Art

In an optical test, for example, in a Raman test, or a florescence test, in order to make the spectrum to be tested have a relative high intensity and a relative high signal-noise ratio, typically, an exciting light needs to be focused. If an object to be inspected is located adjacent to a focal point of a lens, the excitation efficiency will be good. As such, if the object to be inspected is located adjacent to a focal point of a collective lens, signals may be collected into a spectrometer as much as possible. Many optical instruments use a same lens for converging laser light and collect test signals. In this case, whether the object is maintained adjacent to the focal point of the lens or not will significantly affect the test results. In many optical instruments, such as a microscopic Raman spectrometer, or a microscopic florescence spectrometer, typically, an object to be inspected is disposed to be near the focal point of the lens by adjusting a microscopic system. However, adjustment of such a microscopic system is often relatively complicated, and thereby it is only suitable for a research work in a lab. However, poor adjusting efficiency of such microscopic system usually cannot meet the requirement for fast field inspected.

An optical probe, which can focus exciting light onto an object to be inspected and collect light signals containing information of the object, is an important component of an optical inspection instrument.

SUMMARY OF THE INVENTION

An embodiment of the present invention provides an optical probe, comprising:

a first sleeve in which a lens is contained, the first sleeve having a light transmission aperture from which an exciting light enters the first sleeve;

a second sleeve movably engaged with the first sleeve and having a detection window from which the exciting light having passed through the first sleeve and focused by the lens exits the optical probe, the second sleeve being capable of moving with respect to the first sleeve from a first detection position to a second detection position or from the second detection position to the first detection position; and a positioning member configured to position the second sleeve at the first detection position or the second detection position with respect to the first sleeve.

DETAILED DESCRIPTION OF PREFERRED EMBODIMENTS OF THE INVENTION

Figure 1:
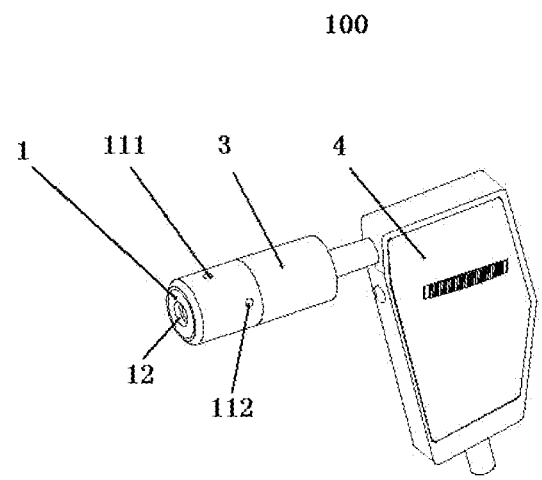
FIG. 1 shows schematically a perspective view of an optical probe according to an embodiment of the present invention, in which a second sleeve is located at a first detection position.
Figure 2:
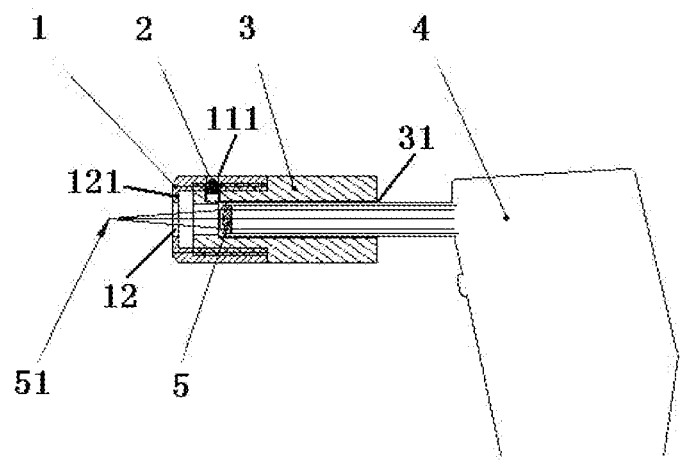
FIG. 2 shows schematically a cross-sectional view of the optical probe shown in FIG. 1.

Exemplary embodiments of the present invention will be described hereinafter in detail with reference to the attached drawings, wherein the like reference numerals refer to the like elements. The present invention may, however, be embodied in many different forms and should not be construed as being limited to the embodiment set forth herein; rather, these embodiments are provided so that the present invention will be thorough and complete, and will fully convey the concept of the disclosure to those skilled in the art.

FIGS. 1-4 show schematically an optical probe 100 according to an embodiment of the present invention. The optical probe 100 may include a first sleeve 3, a second sleeve 1 and a positioning member 2. A lens 5 is contained in the first sleeve 3. The first sleeve 3 has a light transmission aperture 31 through which an exciting light enters the first sleeve 3. The second sleeve 1 is slidably engaged with the first sleeve 3 and has a detection window 12, through which the exciting light having passed through the first sleeve 3 and focused by the lens 5 exits the optical probe 100. The second sleeve 1 is capable of moving with respect to the first sleeve 3 from a first detection position to a second detection position and from the second detection position to the first detection position. The positioning member 2 is configured to position the second sleeve 1 at the first detection position or the second detection position with respect to the first sleeve 3.

Figure 3:
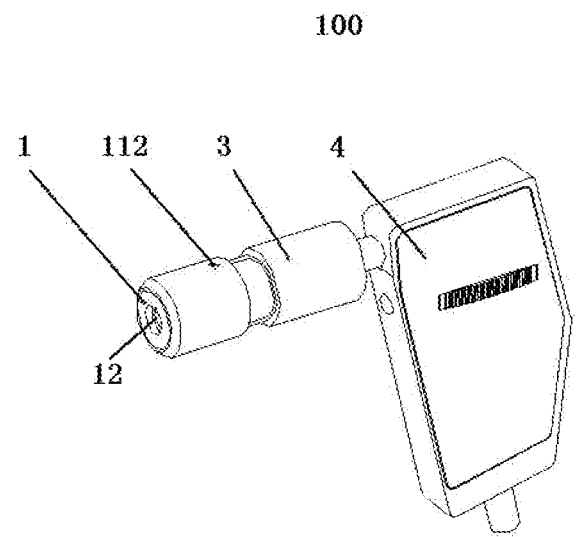
FIG. 3 shows schematically another perspective view of the optical probe shown in FIG. 1, in which the second sleeve is located at a second detection position.
Figure 4:
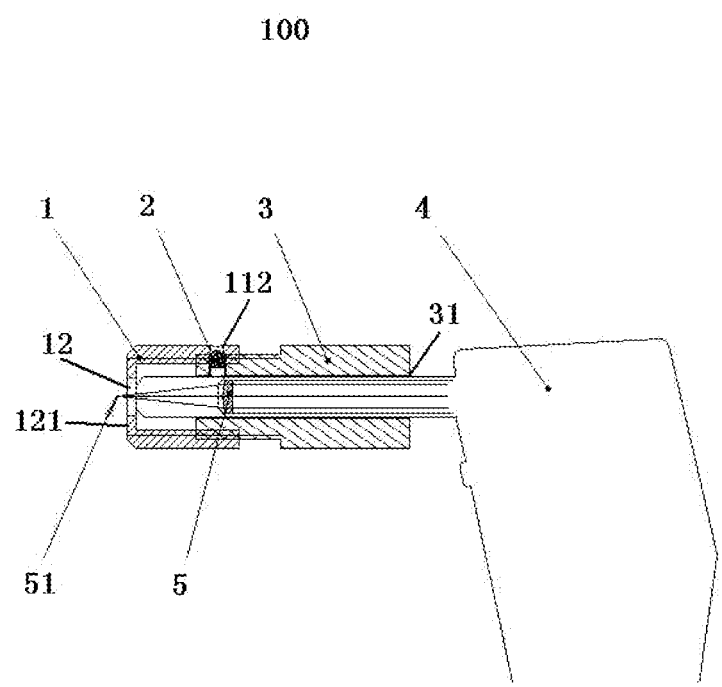
FIG. 4 shows schematically a cross-sectional view of the optical probe shown in FIG. 3.

With a movement, such as rotation or slide, of the second sleeve 1 with respect to the first sleeve 3, the second sleeve 1 may be switched between the extended first detection position (shown in FIGS. 1-2) and the retracted second detection position (shown in FIGS. 3-4). Positional relationships between the detection window 12 of the second sleeve 1 and an optical device (for example. the lens 5) in the first sleeve 3 when the second sleeve 1 is in the first detection position are different from those when the second sleeve 1 is in the second detection position. For example, a distance between the detection window 12 and a focus point 51 of the lens 5 on the side towards the detection window 12 when the second sleeve 1 is at the first detection position is greater than a distance between the detection window 12 and the focus point 51 of the lens 5 on the side towards the detection window 12 when the second sleeve 1 is at the second detection position.

In a practical field inspection, in order to operate conveniently, an outer end face 121 of the second sleeve 1 may be pressed against an object to be inspected, so as to maintain a constant distance between the object and the lens 5 in the first sleeve 3 such that exciting light can be focused stably at a inspection point on the object to acquire a signal. If the object is a massive solid object, the detection window 12 may be directly pressed against the object to perform inspection. In this case, it is desired that the focal point 51 of the lens is located out of the second sleeve 1 and adjacent to the outer end face 121 of the second sleeve 1. Or, if the object is, for example, a gas, liquid, powders or gels hermetically contained in a vessel such as a glass bottle or a plastic bottle, the detection window 12 may be pressed against an outer wall of the vessel allowing the exciting light to pass through the wall of the vessel and to be focused onto the object. In this case, it is desired that the focal point 51 of the lens is located out of the second sleeve 1 and at a certain distance from the outer end face 121 of the second sleeve 1. Thus, as an example, the first detection position and the second detection position of the second sleeve 1 may be configured such that, at the first detection position, the focal point 51 of the lens 5 on the side towards the detection window 12 is located out of the second sleeve 1 and at a certain distance (for example 1-5 cm) from the outer end face 121 of the second sleeve 1 for inspecting an object contained in a vessel; at the second detection position, the focal point 51 of the lens 5 on the side towards the detection window 12 is located out of the second sleeve 1 and adjacent to the outer end face 121 of the second sleeve 1 for inspecting the massive solid object.

In an example, the first sleeve 3 and the second sleeve 1 may be engaged coaxially with each other. For example, the axis of the first sleeve 3 and the axis of the second sleeve 1 are in coincidence with the optical axis of the lens 5. This facilitates adjustment and calibration of the position of the focal point 51 of the lens 5. As an example, the second sleeve 1 may be extended and retracted along the optical axis of the lens 5. However, it is not necessary. For example, the axis of the second sleeve 1 may be orientated at an angle relative to the optical axis of the lens 5, as long as it can ensure that the exciting light may be emitted correctly from the detection window 12.

Figure 5:
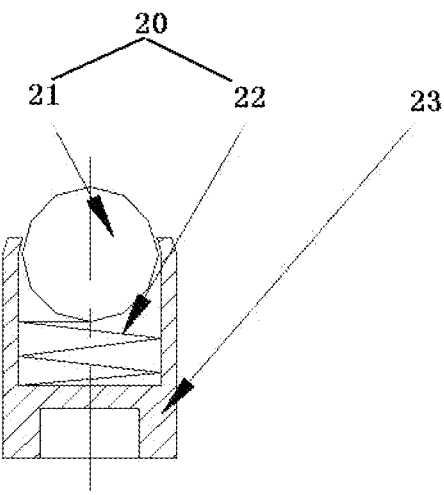
FIG. 5 shows schematically a cross-sectional view of a positioning member according to an embodiment of the present invention.
Figure 6:
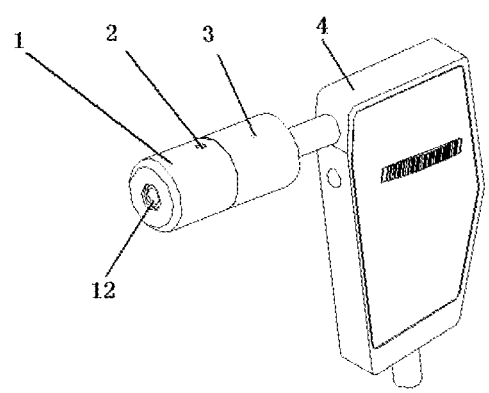
FIG. 6 shows schematically a perspective view of an optical probe according to another embodiment of the present invention, in which a second sleeve is located at a first detection position.
Figure 7:
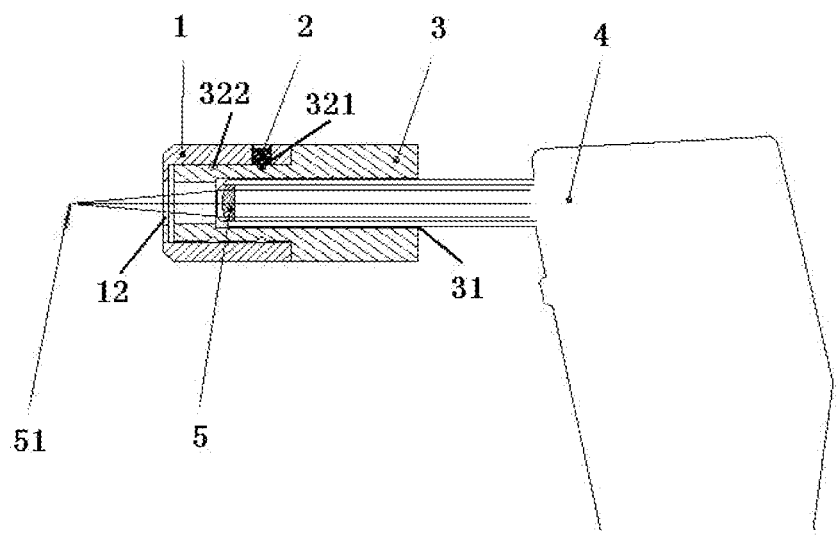
FIG. 7 shows schematically a cross-sectional view of the optical probe shown in FIG. 6.
Figure 8:
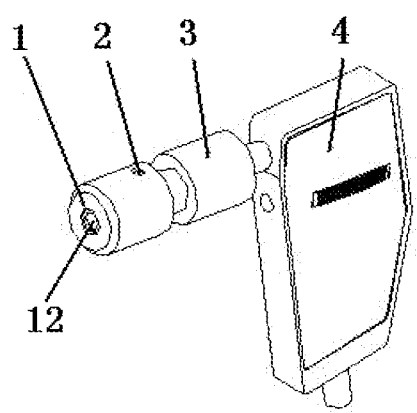
FIG. 8 shows schematically another perspective view of the optical probe shown in FIG. 6, in which the second sleeve is located at a second detection position.
Figure 9:
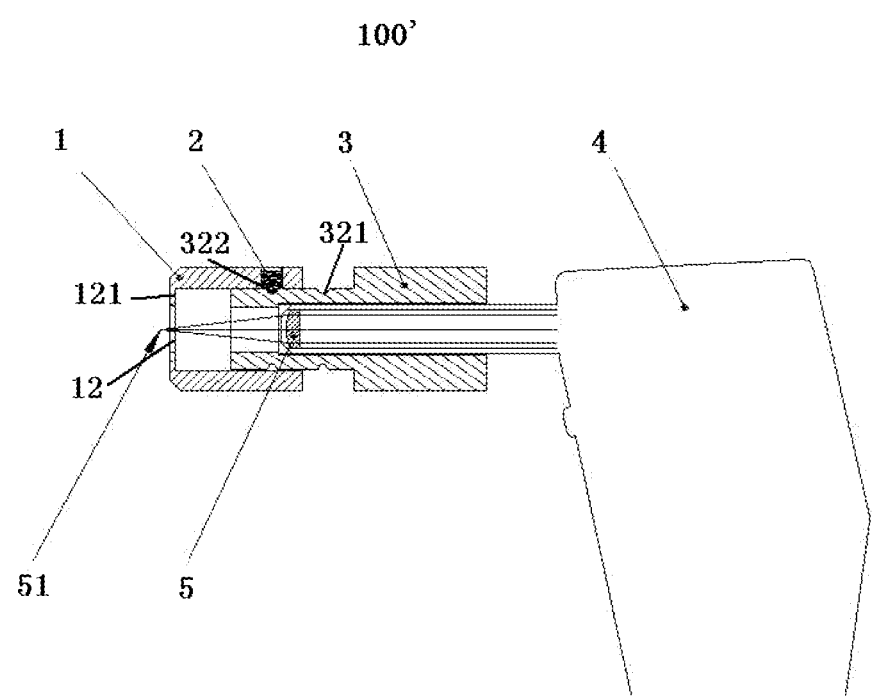
FIG. 9 shows schematically a cross-sectional view of the optical probe shown in FIG. 8.

In an example, the positioning member 2 may have a fixed portion 23 and a retractable portion 20. The fixed portion 23 may be fixed to the first sleeve 3 or the second sleeve 1. FIG. 5 shows an example of the positioning member 2. In the example, the retractable portion 20 includes a ball 21 and a compression spring 22. The fixed portion 23 may be, for example, a plug housing. The fixed portion 23 has a blind hole with an opening. The compression spring 22 is disposed at the bottom of the blind hole and the ball 21 is disposed on the compression spring 22. The diameter of the opening of the blind hole is smaller than the diameter of the ball 21 to prevent the ball 21 from escaping out of the blind hole. When being pressed inward from outside of the blind hole, the ball 21 may compress the compression spring 22 and thereby the upper ball 21 can retract further into the blind hole. Once the pressing action is removed, the ball 21 may be pushed outward by the compression spring 22 and pressed against the opening part of the blind hole to be positioned again at its unretracted position. The ball 21 may be made of metal, such as steel, or may be made of other materials having sufficient hardness, such as plastics. It should be noted that the above description with reference to FIG. 5 only provides an example of the positioning member 2. Instead, other forms of components in the art that can be fitted to the holes or grooves to position the sleeves may also be used in the positioning member 2.

In an embodiment, as illustrated in FIGS. 1-4, the second sleeve 1 is provided with a first positioning hole 111 corresponding to the first detection position and a second positioning hole 112 corresponding to the second detection position. The fixed portion 23 of the positioning member 2 may be fixed to the first sleeve 3. When the second sleeve 1 is at the first detection position, the retractable portion 20 of the positioning member 2 extends into the first positioning hole 111 to lock the position of the second sleeve 1, and when the second sleeve 1 is at the second detection position, the retractable portion 20 extends into the second positioning hole 112 to lock the position of the second sleeve 1. As an example, if the positioning member 2 shown in FIG. 5 is used, the ball 21 will be pushed outward by the compression spring into the first positioning hole 111 when the second sleeve 1 is moved to the first detection position with respect to the first sleeve 3, such that the second sleeve 1 can be held stably at the first detection position; on the other hand, the inner wall of the second sleeve 1 will force the ball 21 to retract into the fixed portion 23 when the second sleeve 1 is moved away from the first detection position. When the second sleeve 1 is moved to the second detection position, the ball 21 will be pushed outward by the compression spring 22 again into the second positioning hole 112, such that the second sleeve 1 can be held stably at the second detection position.

In an example, the first sleeve 3 and the second sleeve 1 are threadedly engaged and are able to rotate with respect to each other through screw threads. In this circumstance, the first positioning hole 111 and the second positioning hole 112 are located along a same screw thread such that the second sleeve 1 can rotate along the same screw thread with respect to the first sleeve 3 to switch between the first detection and the second detection.

As an example, the optical probe 100 may further include an optical fiber coupling device 4 configured to direct a exciting light into the first sleeve 3 and receive light returned from the first sleeve 3. However, the present invention is not limited to this. The optical probe 100 according to an embodiment of the present invention may also include, for example, an optical device composed of separate optical elements, such as lenses, mirrors and prisms. The optical device may also be used to direct exciting light into the first sleeve 3 and receive light returned from the first sleeve 3.

FIGS. 6-9 show an optical probe 100' according to another embodiment of the present invention. Differences between the embodiment shown in FIGS. 6-9 and the embodiment shown in FIGS. 1-4 mainly lie in the connection and positioning structure between the first sleeve 3 and the second sleeve 1. In particular, as shown in FIGS. 6-9, the first sleeve 3 is provided with a first annular positioning groove 321 corresponding to the first detection position and a second annular positioning groove 322 corresponding to the second detection position, and the fixed portion 23 of the positioning member 2 is fixed to the second sleeve 1. When the second sleeve 1 is at the first detection position, the retractable portion 20 of the positioning member 2 extends into the first annular positioning groove 321 to lock the position of the second sleeve 1, and when the second sleeve 1 is at the second detection position, the retractable portion 20 extends into the second annular positioning groove 322 to lock the position of the second sleeve 1. As an example, if the positioning member 2 as shown in FIG. 5 is used, the ball 21 will be pushed outward by the compression spring 22 into the first annular positioning groove 321 when the second sleeve 1 is moved to the first detection position with respect to the first sleeve 3, such that the second sleeve 1 can be held stably at the first detection position; on the other hand, the wall of the second sleeve 1 will force the ball 21 to retract into the fixed portion 23 when the second sleeve 1 is moved away from the first detection position. When the second sleeve 1 is moved to the second detection position, the ball 21 will be pushed outward by the compression spring 22 again into the second annular positioning groove 322, such that the second sleeve 1 can be held stably at the second detection position.

In the embodiment shown in FIGS. 6-9, the first sleeve 3 and the second sleeve 1 are engaged through polygonal fitting surfaces. That is to say, the fitting portion for engaging the first sleeve 3 and the second sleeve 1 with each other has a polygonal cross section, for example, a triangular cross section, a rectangular cross section, a pentagonal cross section, a hexagonal cross section or the like. With such polygonal fitting surfaces, the first sleeve 3 and the second sleeve 1 are not rotatable but axially slidable with respect to each other in contrast to the examples discussed above with references to FIGS. 1-5. Thus, the second sleeve 1 may be moved more conveniently with respect to the first sleeve 3. With the positioning member 2 and the sliding engagement between the first sleeve 3 and the second sleeve 1, the second sleeve 1 can be switched between the first detection position and the second detection position by axially sliding relative to the first sleeve 3. For example, the second sleeve 1 can be actuated directly by a hand of the operator. In an example, the first annular positioning groove 321 and the second annular positioning groove 322 may be parallel to each other. It may allow the positioning member 2 to position the second sleeve 1 in the same manner at any position on the circumference of the first sleeve 3, and thereby assembly and calibration process is simplified.

Other features in the embodiment shown in FIGS. 6-9 are the same as those in the previous embodiment shown in FIGS. 1-4. Thus, the specific explanations to these features will be omitted.

In the above embodiments, the lens 5 may have a fixed focal length, because the change of position of the focal point 51 of the lens 5 does not depends on the change of the focal length. Of course, the lens 5 may also have a variable focal length.

In the above embodiments, axial travel length of the second sleeve 1 with respect to the first sleeve 3 may be, for example, 0.5-10 cm, such as 1-5 cm.

It should be noted that, although the above embodiments of the present invention are described with reference to two detection positions, the optical probes 100, 100' according to the embodiments of the present invention may also provide more detection positions to meet the requirements for various measurement applications. For example, a third detection position, a fourth detection position, and a fifth detection position may be provided between the first detection position and the second detection position. In such circumstances, a third positioning hole, a fourth positioning hole, and a fifth positioning hole, or a third annular positioning groove, a fourth annular positioning groove, and a fifth annular positioning groove may be provided correspondingly.

The optical probe according to the embodiments of the present invention may be applied in a Raman inspection, a florescence inspection or other various applications of optical inspection.

Although the present invention has been explained with reference to the drawings, the embodiments shown in the drawings are only illustrative, instead of limiting the present invention.

Although some embodiments of the general inventive concept are illustrated and explained, it would be appreciated by those skilled in the art that modifications and variations may be made in these embodiments without departing from the principles and spirit of the general inventive concept of the disclosure, the scope of which is defined in the appended claims and their equivalents.

What is claimed is:

1. An optical probe, comprising:
   a first sleeve in which a lens is contained, the first sleeve having a light transmission aperture from which an exciting light enters the first sleeve;
   a second sleeve movably engaged with the first sleeve and having a detection window from which the exciting light having passed through the first sleeve and focused by the lens exits the optical probe, the second sleeve being capable of moving with respect to the first sleeve from a first detection position to a second detection position or from the second detection position to the first detection position; and
   a positioning member configured to position the second sleeve at the first detection position or the second detection position with respect to the first sleeve.

2. The optical probe according to claim 1, wherein a distance between the detection window and a focus point of the lens on the side towards the detection window when the second sleeve is at the first detection position is greater than a distance between the detection window and the focus point of the lens on the side towards the detection window when the second sleeve is at the second detection position.

3. The optical probe according to claim 2, wherein when the second sleeve is at the second detection position, the focus point of the lens on the side towards the detection window is located out of the second sleeve and adjacent to an outer end face of the second sleeve.

4. The optical probe according to claim 1, wherein the positioning member has a fixed portion which is fixed to the first or the second sleeve and a retractable portion.

5. The optical probe according to claim 1, wherein the first sleeve and the second sleeve are coaxially engaged with each other.

6. The optical probe according to claim 1, wherein the second sleeve is provided with a first positioning hole corresponding to the first detection position and a second positioning hole corresponding to the second detection position, the positioning member having a fixed portion which is fixed to the first sleeve and a retractable portion, and wherein the retractable portion extends into the first positioning hole when the second sleeve is at the first detection position to fix the second sleeve, and the retractable portion extends into the second positioning hole when the second sleeve is at the second detection position to fix the second sleeve.

7. The optical probe according to claim 6, wherein the first sleeve and the second sleeve are threadedly engaged with each other and are able to rotate with respect to each other along screw threads, the first positioning hole and the second positioning hole being located along a same screw thread.

8. The optical probe according to claim 1, wherein the first sleeve is provided with a first annular positioning groove corresponding to the first detection position and a second annular positioning groove corresponding to the second detection position, the positioning member having a fixed portion which is fixed to the second sleeve and a retractable portion, and wherein the retractable portion extends into the first annular positioning groove when the second sleeve is at the first detection position to fix the second sleeve, and the retractable portion extends into the second annular positioning groove when the second sleeve is at the second detection position to fix the second sleeve.

9. The optical probe according to claim 8, the first sleeve and the second sleeve are engaged with each other through polygonal fitting surfaces, the first annular positioning groove and the second annular positioning groove being parallel to each other.

10. The optical probe according to claim 1, further comprising an optical fiber coupling device or an optical device configured to direct the exciting light into the first sleeve and receive the light back from the first sleeve, wherein the optical device is composed of separate optical elements.

\* \* \* \* \*